US012584124B2

(12) United States Patent
Boey et al.

(10) Patent No.: US 12,584,124 B2
(45) Date of Patent: Mar. 24, 2026

(54) MAGNETIC BEAD BASED NUCLEIC ACID EXTRACTION SYSTEM

(71) Applicant: Delta Electronics Int'l (Singapore) Pte Ltd, Singapore (SG)

(72) Inventors: Jia Hui Esther Boey, Singapore (SG); Weishi Zhang, Singapore (SG); Casthri Krishnamurthy, Singapore (SG)

(73) Assignee: Delta Electronics Int'l (Singapore) Pte Ltd, Singapore (SG)

( * ) Notice: Subject to any disclaimer, the term of this patent is extended or adjusted under 35 U.S.C. 154(b) by 446 days.

(21) Appl. No.: 18/143,675

(22) Filed: May 5, 2023

(65) Prior Publication Data

US 2024/0368581 A1      Nov. 7, 2024

(51) Int. Cl.
*C12N 15/10*      (2006.01)
(52) U.S. Cl.
CPC ................................ *C12N 15/1013* (2013.01)
(58) Field of Classification Search
None
See application file for complete search history.

(56) References Cited

U.S. PATENT DOCUMENTS

| | | | |
|---|---|---|---|
| 5,234,809 A | 8/1993 | Boom et al. |
| 6,582,922 B1 | 6/2003 | Daimon et al. |
| 9,976,136 B2 | 5/2018 | Fischer et al. |
| 10,072,259 B2 | 9/2018 | Gundling |
| 2001/0018513 A1 | 8/2001 | Baker |
| 2004/0137449 A1 | 7/2004 | Nargessi |
| 2010/0029925 A1 | 2/2010 | Brevnov et al. |
| 2011/0092687 A1 | 4/2011 | Bendzko et al. |
| 2018/0355346 A1 | 12/2018 | Hsieh et al. |
| 2021/0054363 A1 | 2/2021 | Koetsier et al. |

FOREIGN PATENT DOCUMENTS

| | | |
|---|---|---|
| CN | 102911932 A | 2/2013 |
| CN | 103820431 A | 5/2014 |
| CN | 109722431 A | 5/2019 |
| CN | 112980830 A | 6/2021 |
| CN | 113249188 A | 8/2021 |
| CN | 113462683 A | 10/2021 |
| CN | 114164206 A | 3/2022 |
| EP | 1510577 A1 | 3/2005 |
| WO | 0034463 A1 | 6/2000 |

OTHER PUBLICATIONS

Kim, YeJi, et al. "Direct buffer composition of blood pre-process for nucleic acid based diagnostics." Biochip journal 11.4 (2017): 255-261.*
Miller SA et al., A simple salting out procedure for extracting DNA from human nucleated cells, Nucleic Acids Res. Feb. 11, 1988; 16(3): 1215.

* cited by examiner

*Primary Examiner* — Patrick T Lewis
(74) *Attorney, Agent, or Firm* — KIRTON McCONKIE; Evan R. Witt

(57)      ABSTRACT

A magnetic bead based nucleic acid extraction system includes a plurality of magnetic beads and an alcohol-free buffer system. The alcohol-free buffer system includes a lysis binding buffer, a first wash buffer, a second wash buffer, and an elution buffer that are stable in storage at room temperature. The buffers include a special selection of chaotropic salt, detergent, precipitant and other necessary components for ideal extraction of nucleic acids. The magnetic bead based nucleic acid extraction system is stable, user-friendly and environment-friendly, efficient and efficacious nucleic acid extraction system optimal for pathogens from swab samples, and can achieve efficient both DNA and RNA extractions, be it separately or simultaneously, from both virus and bacteria in swab samples.

8 Claims, 22 Drawing Sheets

| Buffer Set A | | |
| Sample | Cq | Cq mean |
| OC43 | 24.28 | 24.19 |
| OC43 | 24.10 | |
| OC43 | 24.19 | |

| Buffer Set A | | |
| --- | --- | --- |
| Sample | Cq | Cq mean |
| Ad3 | 26.77 | 26.67 |
| Ad3 | 26.64 | |
| Ad3 | 26.59 | |

| Buffer Set B | | |
|---|---|---|
| Sample | Cq | Cq mean |
| OC43 | 33.44 | 33.54 |
| OC43 | 33.08 | |
| OC43 | 34.10 | |

| Buffer Set B | | |
| Sample | Cq | Cq mean |
| SA | 32.44 | 32.63 |
| SA | 32.91 | |
| SA | 32.53 | |

| | Buffer Set B | |
|---|---|---|
| Sample | Cq | Cq mean |
| Ad3 | 33.70 | 35.66 |
| Ad3 | 35.50 | |
| Ad3 | 37.78 | |

| Buffer Set C | | |
|---|---|---|
| Sample | Cq | Cq mean |
| OC43 | 33.22 | 33.18 |
| OC43 | 34.05 | |
| OC43 | 32.27 | |

| Buffer Set C | | |
| --- | --- | --- |
| Sample | Cq | Cq mean |
| SA | 32.45 | 32.38 |
| SA | 32.26 | |
| SA | 32.43 | |

| | Buffer Set C | |
| --- | --- | --- |
| Sample | Cq | Cq mean |
| Ad3 | 34.06 | |
| Ad3 | 33.86 | 33.82 |
| Ad3 | 33.54 | |

| Sample | Cq | Cq mean |
|--------|-------|---------|
| OC43 | 17.28 | 17.18 |
| OC43 | 17.49 | |
| OC43 | 16.77 | |

| Sample | Cq | Cq mean |
|---|---|---|
| OC43 | 29.90 / 29.86 | 29.88 |
| OC43 | 29.78 / 29.81 | 29.80 |
| OC43 | 29.65 / 29.70 | 29.67 |

| Sample | Cq | Cq mean |
|---|---|---|
| SA | 28.66 | 28.57 |
| | 28.48 | |
| SA | 29.10 | 29.06 |
| | 29.02 | |
| SA | 28.66 | 28.60 |
| | 28.54 | |

| Sample | Cq | Cq mean |
|---|---|---|
| 1.5x10^-4 | 36.27 | 35.88 |
| | 35.48 | |
| 10^-3 | 32.96 | 33.21 |
| | 33.45 | |
| 10^-2 | 30.83 | 31.13 |
| | 31.43 | |

| Sample | Cq | Cq mean |
|--------|-------|---------|
| 15 | 36.75 | 36.82 |
| | 36.88 | |
| 100 | 34.30 | 34.29 |
| | 34.27 | |
| 1000 | 30.62 | 30.65 |
| | 30.68 | |

| Sample | Cq | | Cq mean |
|---|---|---|---|
| Present Protocol (P) | 39.48 | | 38.50 |
| | 38.03 | | |
| | 38.00 | | |
| Katsura (K) | 37.39 | N/A | 38.42/NA |
| | N/A | | |
| | 39.45 | | |
| Macherey-Nagel (M) | N/A | N/A | N/A |
| | N/A | | |
| | N/A | | |

| Sample | Cq | Cq mean |
| --- | --- | --- |
| Present Protocol (P) | 37.15 | 36.93 |
| | 36.75 | |
| | 36.88 | |
| Katsura (K) | 38.58 | 39.59 |
| | 40.23 | |
| | 39.96 | |

| Step | Present protocol | Katsura DNA/RNA Respi kit | MN NucleoMag Pathogen kit |
|---|---|---|---|
| Lysis | 4min | 5min | 50min |
| Mag | 1min | 10s | 2min |
| Wash 1 | 10s | 1min | 1min |
| Mag | 30s | 10s | 2min |
| Wash 2 | 10s | 1min | 1min |
| Mag | 30s | 10s | 2min |
| Elution | 2min | 5min | 1min |
| Standby | - | 5min | 10min |
| Mag | 30s | 30s | 2min |
| Total time | 9mins | 18mins | 71mins |

FIG. 16

| | Features | Present protocol | MN NucleoMag Pathogen kit | QIAamp Viral RNA Mini kit | Katsura DNA/RNA Respi kit |
|---|---|---|---|---|---|
| Reagent simplicity | Ethanol/isopropanol-free | ✓ | ✗ | ✗ | ✗ |
| | Proteinase K-free | ✓ | ✗ | ✓ | ✓ |
| | Enzyme-free | ✓ | ✗ | ✓ | ✓ |
| | Storage | Room temperature | Room temperature and -20°C | Room temperature and -20°C | Room temperature |
| | Pre-treatment required? | No | Yes | No | No |
| Protocol simplicity | Operational temperature | Room temperature and 80°C | Room temperature and 56°C | Room temperature | Room temperature and 80°C |
| | No centrifugation | ✓ | ✓ | ✗ | ✓ |
| | No beads drying step | ✓ | ✗ | ✓ | ✗ |
| | Number of steps | 8 | 18 | 12 | Automated |
| Targets | Virus RNA/DNA | ✓ | ✓ | ✓ | ✓ |
| | Bacteria DNA | ✓ | ✓ | ✗ | ✗ |
| Time taken | Total protocol time | 9mins | 71mins | 23mins | 18mins |

FIG. 17

| Bead | Cq mean |
|------|---------|
| A | 32.48 |
| B | 32.81 |
| C | 32.97 |
| D | 31.32 |
| E | 32.58 |
| F | 33.47 |
| G | 32.08 |

| Bead | Cq mean |
|------|---------|
| H | 33.41 |
| I | 33.14 |
| J | 33.97 |

| Copies / PCR | Cq mean |
|---|---|
| 10000 | 26.60 |
| 1000 | 32.20 |
| 100 | 34.54 |
| 10 | 37.86 |

| Extraction Method | Present Protocol on M32 machine | | |
|---|---|---|---|
| Sample Volume | 300 μl | | |
| Elution Volume | 80 μl | | |
| Copies / reaction | Cq mean | Recovery (copies) | Recovery (%) |
| 10^4 | 26.85 | 8503.54 | 85.04 |
| 10^3 | 30.13 | 1172.74 | 117.27 |
| 10^2 | 33.57 | 146.82 | 146.82 |
| 10 | 39.64 | 3.75 | 37.54 |

| Extraction Method | Qiagen viral RNA kit | | |
|---|---|---|---|
| Sample Volume | 300 μl | | |
| Elution Volume | 80 μl | | |
| Copies / reaction | Cq mean | Recovery (copies) | Recovery (%) |
| 10^4 | 26.66 | 9538.94 | 95.39 |
| 10^3 | 30.21 | 1117.38 | 117.74 |
| 10^2 | 33.64 | 140.73 | 140.73 |
| 10 | 40.02 | 2.98 | 29.84 |

FIG. 20

MAGNETIC BEAD BASED NUCLEIC ACID EXTRACTION SYSTEM

FIELD OF THE INVENTION

The present disclosure relates to a nucleic acid extraction system, and more particularly to a magnetic bead based nucleic acid extraction system.

BACKGROUND OF THE INVENTION

Nucleic acid detection is the latest advancement in molecular diagnosis with superior sensitivity and specificity. It has been widely used in various fields such as inheritance disease study, oncology and epidemiology of infectious diseases. Nucleic acid extraction is the prerequisite for sensitive target detection. Major functions of nucleic acid extraction are to get nucleic acids of high qualities and to remove inhibitory factors presented in sample matrices. Many methods have been developed based on different extraction mechanisms. Existing methods can be roughly categorized into two groups: chemically driven methods and solid phase based methods.

Chemically driven methods are earlier development based on phase separation of phenol-chloroform in solutions and precipitation of nucleic acids by alcohols, e.g., isopropanol and ethanol. Cell lysis happens under strong protein denaturing components such as sodium dodecyl sulfate (SDS) and proteinase K. A mixture of phenol:chloroform:isoamyl alcohol (25:24:1) is then added to facilitate phase separation of DNA, lipids and other cellular debris. DNA is in the aqueous phase and the rest are in the organic phase. Under centrifugal forces, DNA containing aqueous phase on top of the organic phase can be transferred to a clean tube for analysis or DNA can also be further recovered and concentrated by ethanol precipitation. However, there are several disadvantages associated with this method. Firstly, it is very time-consuming and requires considerable efforts. In addition, the procedures pose high risk of damage to operators due to carcinogenic and toxic chemicals such as chloroform or phenol. Furthermore, for the extracted nucleic acids, there is a risk of phenol contamination and an increased content of so-called "nicked" nucleic acid at many sites, which in turn highly affects stability of the extracted nucleic acids. In addition, the containing of ethanol will cause inconvenience and high cost in reagent transportation and storage.

An alternative to the phenol-chloroform extraction procedure is the salting-out method based on the principle that proteins and other cellular contaminants will precipitate in a saturated salt solution due to their relative hydrophobicity, while DNA does not. After cell lysis, a saturated salt solution such as 6 M sodium chloride (NaCl) is added. A well-mixed cell lysate-salt solution is then subjected to centrifugation to precipitate protein matters. The supernatant contains DNA, which can be transferred to a new tube and combined with a 2× volume of pure ethanol to allow further DNA precipitation and purification. This method avoids usage of toxic organic chemicals. However, it is not uncommon that the salt used for protein precipitation may contaminate the extracted nucleic acids which in turn inhibit enzymatic nucleic acid amplification such as PCR or other isothermal based methods.

A later development is to introduce solid phase of various materials to selectively bind nucleic acids, which realizes one-vessel nucleic acid extraction compared to usage of multiple vessels in the traditional extraction methods based on phase separation and salting-out mechanisms. As functionality of the solid phase is affected by solutions coming into contact, be it lysis buffer, binding buffer, wash buffer and elution buffer, buffer formulation is also an important part for an efficient nucleic acid extraction system. The solid phase used to bind nucleic acids may be carrier materials, spin filters, silica particles, cuvettes, microtiter plates, filter membranes, polystyrene beads and nitrocellulose paper, and many methods are developed correspondingly.

The aforementioned methods, no matter they are based on solution phase separation or solid phase separation, centrifuge is a must-have piece of equipment, which hinders high level of automation for sample preparation. The most recent development in nucleic acid extraction is to include magnetic beads which can be functionalized by different motifs to selectively bind nucleic acids, realizing rapid and high level of automation for nucleic acid extraction.

Convenient and efficient nucleic acid extraction has been made technology advancement in biological and molecular science in the forms of kits made up of special devices and associated buffers. However, there are several challenges yet to address. Firstly, most commercially available nucleic extraction kits call for a list of consumables and/or equipment to be provided by end-users, which can only be satisfied by well-facilitated labs. Secondly, alcohol or isopropanol are important components of the buffers for the aforementioned most recent development where functionalized magnetic beads are used as carriers to specifically capture nucleic acids. When put on cartridge for point of care (POC) applications, alcohols can react with plastic materials, undermining their mechanical/physiochemical properties. They can also be problematic due to their volatility, flammability and potential to leak. Such properties make alcohols a substance highly regulated by International Air Transport Association (IATA). Thirdly, turn-around time for most commercial kits is longer than half an hour. Fourthly, most of the extraction buffers can only be used to extract either DNA or RNA from either virus or bacteria. There is lacking of a universal buffer system which can effectively extract and purify all nucleic acids from pathogens in human swab samples. Last, special components in some extraction buffers require-20° C. or 4° C. cold/cool storage for desired performance, especially for those kits containing proteinase for cell lysis and nuclease denaturation and carrier nucleic acid for low quantity of template input, causing inconvenience in shipping and storage.

Therefore, there is a need of providing a nucleic acid extraction system to address the challenges encountered in the prior arts.

SUMMARY OF THE INVENTION

An object of the present disclosure is to provide a magnetic bead based nucleic acid extraction system which is a stable, user-friendly and environment-friendly, efficient and efficacious nucleic acid extraction system optimal for pathogens from swab samples.

Another object of the present disclosure is to provide a magnetic bead based nucleic acid extraction system which is alcohol-free, so as to obviate the problems caused by the alcohol.

An additional object of the present disclosure is to provide a magnetic bead based nucleic acid extraction system which achieves efficient both DNA and RNA extractions, be it separately or simultaneously, from both virus and bacteria in swab samples.

In accordance with an aspect of the present disclosure, a magnetic bead based nucleic acid extraction system is provided. The magnetic bead based nucleic acid extraction system includes a plurality of magnetic beads and an alcohol-free buffer system. The alcohol-free buffer system includes a lysis binding buffer, a first wash buffer, a second wash buffer, and an elution buffer. The lysis binding buffer includes 0.5 to 4 M GuSCN, 5 to 20% (v/v) PEG8000, 10 to 1000 mM sodium citrate, and a non-ionic detergent selected from the group consisting of 0.5 to 4% (v/v) nonylphenyl polyethylene glycol (NP-40 alternative, CAS number: 9016-45-9), 0.5 to 4% (v/v) secondary alcohol ethoxylate (Tergitol 15-S-40, CAS number: 84133-50-6), 0.5 to 4% (v/v) ethylene oxide-propylene oxide copolymer mono(2-ethylhexyl) ether (Ecosurf EH-9, CAS number: 64366-70-7) and mixtures thereof. The first wash buffer includes 0.5 to 3 M GuSCN, 5 to 20% (v/v) PEG8000, 0.5 to 2 M sodium chloride, 5 to 25 mM EDTA, and a non-ionic detergent selected from the group consisting of 0.25 to 4% (v/v) Ecosurf EH-9, 0.1 to 4% (v/v) 2-[4-(2,4,4-trimethyl-pentan-2-yl)phenoxy]ethanol (Triton X-100, CAS number: 9002-93-1), 0.25 to 4% (v/v) Tergitol 15-S-40 and mixtures thereof. The second wash buffer includes 1 to 25 mM hexammine cobalt (III) chloride, 5 to 20% (v/v) PEG8000, 5 to 1000 mM sodium chloride, and a non-ionic detergent selected from the group consisting of 0.25 to 2% (v/v) Ecosurf EH-9, 0.1 to 2% (v/v) Triton X-100, 0.25 to 2% (v/v) Tergitol 15-S-40 and mixtures thereof.

In an embodiment, the pH value of the lysis binding buffer is 3 to 5.

In an embodiment, the pH value of the first wash buffer is 3 to 5.

In an embodiment, the first wash buffer further includes 0.01 to 1% (v/v) lactic acid.

In an embodiment, the pH value of the second wash buffer is 3 to 5.

In an embodiment, the second wash buffer further includes 0.01 to 1% (v/v) lactic acid.

In an embodiment, the pH value of the elution buffer is 8.

In an embodiment, the elution buffer includes 1 to 25 mM EDTA.

The above contents of the present disclosure will become more readily apparent to those ordinarily skilled in the art after reviewing the following detailed description and accompanying drawings, in which:

BRIEF DESCRIPTION OF THE DRAWINGS

FIG. 16 shows the comparison of nucleic acid extraction protocol turn-around-time for the present protocol and the leading commercial kits;

FIG. 17 shows the feature comparison for the present protocol and the leading commercial kits;

FIG. 20 shows the yield comparison using Vircell RNA with the present protocol on the automated nucleic acid extractor with the leading commercial kit.

DETAILED DESCRIPTION OF THE PREFERRED EMBODIMENT

Figure 1:
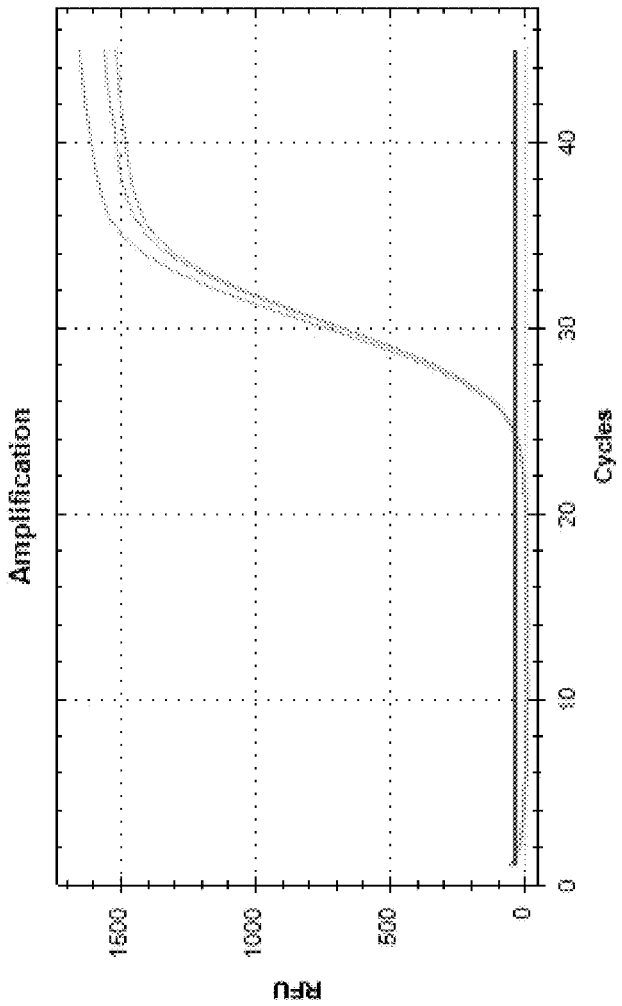
FIG. 1 shows the amplification curves and Cq values of the qPCR assay in Example 1.

The present disclosure will now be described more specifically with reference to the following embodiments. It is to be noted that the following descriptions of the embodiments of this disclosure are presented herein for purpose of illustration and description only; it is not intended to be exhaustive or to be limited to the precise form disclosed.

The present disclosure is to provide a stable, user-friendly and environment-friendly, efficient and efficacious total nucleic acid extraction and purification system optimal for both viruses and bacteria in swab samples. The system includes buffers, magnetic beads and a protocol for nucleic acid extraction from swab samples. The system is capable of lysis of the starting material, binding of the nucleic acids to magnetic beads, washing of impurities and elution of the nucleic acids from the magnetic beads. The associated protocol was optimized to achieve efficient both DNA and RNA extraction, be it separately or simultaneously, from pathogens in swab samples.

Accordingly, the present disclosure provides a nucleic acid extraction and purification system which employs the solid phase based mechanism, particularly the magnetic separation. The magnetic separation uses magnetic beads, preferably paramagnetic beads, to extract out nucleic acids in the cell lysates based on that the magnetic beads can bind nucleic acids reversibly by just adjusting buffer conditions. The magnetic separation has no centrifugation step and does not need to remove supernatants or exchange containers, allowing full automation of the extraction process.

In the conventional magnetic separation techniques, alcohol is used in most wash buffers, and also used in lysis buffer or elution buffer in some protocols. However, it is problematic due to its volatility, flammability, potential to leak, and alcohol-shipping restrictions in many countries. Therefore, the buffer system in the present disclosure is designed to be alcohol-free, so as to obviate the problems caused by the alcohol. Briefly, the magnetic bead based nucleic acid extraction system of the present disclosure includes a plurality of magnetic beads and an alcohol-free buffer system. The buffer system includes a lysis binding buffer, a wash buffer and an elution buffer, and these buffers are described in detail as follows.

The lysis binding buffer is used for lysis of the sample and binding of the nucleic acids to the magnetic beads by combined action of a detergent, a chaotropic salt, a precipitant and a salt at optimal pH.

The detergent disrupts structure of lipid-biolayer and some proteins in the microbe membrane, which compromises membrane integrity and facilitates cell lysis. Depending on molecular structures, there are four types of detergents: anionic detergents, cationic detergents, non-ionic detergents and zwitter ionic detergents. In the present disclosure, the non-ionic detergent is used in the lysis binding buffer.

In an embodiment, the non-ionic detergent is selected from the group consisting of NP-40 alternative (excluding NP-40), Tergitol 15-S-40, Ecosurf EH-9 and mixtures thereof. The concentrations are 0.5 to 4% (v/v), preferably 0.8 to 1% (v/v), for NP-40 alternative, 0.5 to 4% (v/v), preferably 0.5 to 1.25% (v/v), for Tergitol 15-S-40, and 0.5 to 4% (v/v), preferably 0.5 to 1.25% (v/v), for Ecosurf EH-9. Three sets of the lysis binding buffers are available, formulated with either NP-40 alternative, Tergitol 15-S-40 or Ecosurf EH-9.

The chaotropic salt is capable of protein denaturation due to its ability to disrupt hydrophobic interactions. The chaotropic salt helps with lysis of the cell membrane, inactivation of nucleases, and promotion of nucleic acid binding to the magnetic beads. In an embodiment, guanidine thiocyanate (GuSCN), one of the most potent chaotropes, is used in the lysis binding buffer of the present disclosure, and the concentration for GuSCN is 0.5 to 4 M, preferably 1 to 3 M.

DNA or RNA precipitation is important for nucleic acid separation from other components of the sample. Several mechanisms can be employed and the most prominent two are decreasing repulsion of these macromolecules as in the case of multivalent cations and making interaction between nucleic acids and water molecules less favorable. Alcohol is an efficient precipitant to decrease favorable interaction between nucleic acids and water molecules, but it is problematic as described above.

In the present disclosure, an alcohol-free precipitant is used in the lysis binding buffer. In an embodiment, the precipitant includes high molecular weight PEG8000 at 5 to 20% (v/v), preferably 5 to 10% (v/v), with suitable salt of sodium citrate at concentration of 10 to 1000 mM, preferably 10 to 50 mM, to efficiently condense the nucleic acids from the sample, where the latter also helps to chelate metal ions which activate DNase and RNase enzymes. In some embodiments, the PEG8000 may be substituted by other PEG with different molecular weights.

Aside from reasonable choice of chemicals and determination of their optimal concentrations, another important factor is buffer pH. The magnetic beads are specially manufactured to have functional moieties on the surface to specifically attach and detach the nucleic acids. This functionality depends on pH of the buffers. The pH of the lysis binding buffer is 3 to 5 provided by Tris-acetate with the concentration of 5 to 100 mM, preferably 5 to 20 mM, at which highest binding ability was noticed from the magnetic beads.

Therefore, as described above, the lysis binding buffer used in the present magnetic bead based nucleic acid extraction system includes 0.5 to 4 M GuSCN, 5 to 20% (v/v) PEG8000, 10 to 1000 mM sodium citrate, and a non-ionic detergent selected from the group consisting of 0.5 to 4%

(v/v) NP-40 alternative, 0.5 to 4% (v/v) Tergitol 15-S-40, 0.5 to 4% (v/v) Ecosurf EH-9 and mixtures thereof. The pH value of the lysis binding buffer is adjusted to 3 to 5 with concentrated acetic acid. The three sets A, B and C of the lysis binding buffers are shown in the following Table 1 to Table 3.

TABLE 1

| Lysis Binding Buffer Set A | |
| --- | --- |
| Component | Concentration range |
| Tris-acetate (pH3 to 5) | 5 to 100 mM |
| GuSCN | 0.5 to 4M |
| PEG 8000 | 5 to 20% (v/v) |
| Ecosurf EH-9 | 0.5 to 4% (v/v) |
| Sodium Citrate | 10 to 1000 mM |

TABLE 2

| Lysis Binding Buffer Set B | |
| --- | --- |
| Component | Concentration range |
| Tris-Acetate (pH3 to 5) | 5 to 100 mM |
| GuSCN | 0.5 to 4M |
| PEG 8000 | 5 to 20% (v/v) |
| NP-40 alternative | 0.5 to 4% (v/v) |
| Sodium Citrate | 10 to 1000 mM |

TABLE 3

| Lysis Binding Buffer Set C | |
| --- | --- |
| Component | Concentration range |
| Tris-Acetate (pH3 to 5) | 5 to 100 mM |
| GuSCN | 0.5 to 4M |
| PEG 8000 | 5 to 20% (v/v) |
| Tergitol 15-S-40 | 0.5 to 4% (v/v) |
| Sodium Citrate | 10 to 1000 mM |

The wash buffer is used to remove impurity present in the sample from the nucleic acids. As the nucleic acids are bound to the magnetic beads, the wash buffer while removing impurity must have the property to minimally disrupt the bound nucleic acids on the magnetic beads. At least two wash buffers are used in the present magnetic bead based nucleic acid extraction system. Each of the wash buffers includes a detergent, a chaotropic salt, a precipitant, a chelating agent, and a salt at optimal pH.

In the present disclosure, the non-ionic detergent is used in the wash buffers to help remove impurities. In an embodiment, the non-ionic detergent is selected from group consisting of Ecosurf EH-9, Triton X-100, Tergitol 15-S-40, and mixtures thereof. The concentrations are 0.25 to 4% (v/v), preferably 0.5 to 1.25% (v/v), for Ecosurf EH-9, 0.1 to 4% (v/v), preferably 0.1 to 2% (v/v), for Triton X-100, and 0.25 to 4% (v/v), preferably 0.5 to 1% (v/v), for Tergitol 15-S-40 in the first wash buffer of the present disclosure, while the concentrations are 0.25 to 2% (v/v), preferably 0.25 to 0.75% (v/v), for Ecosurf EH-9, 0.1 to 2% (v/v), preferably 0.1 to 1% (v/v), for Triton X-100, and 0.25 to 2% (v/v), preferably 0.25 to 0.75% (v/v), for Tergitol 15-S-40 in the second wash buffer of the present disclosure. Three sets of the wash buffers are available, formulated with either Triton X-100, Tergitol 15-S-40 or Ecosurf EH-9.

In an embodiment, the pH value of the wash buffers is 3 to 5 provided by Tris-HCl with the concentration of 10 to 100 mM and is determined to be optimal for sustaining the binding of the nucleic acids on the magnetic beads. Optionally, lactic acid may also be added into the wash buffers for adjusting the pH value of the wash buffers, and the concentration of lactic acid is 0.01 to 1% (v/v), preferably 0.01 to 0.5% (v/v), in the wash buffers.

In an embodiment, guanidine thiocyanate (GuSCN), one of the most potent chaotropes, is used in the first wash buffer of the present disclosure, and the concentration for GuSCN is 0.5 to 3 M, preferably 1 to 2 M. While in the second wash buffer, hexammine cobalt (III) chloride is used at 1 to 25 mM, preferably 1 to 5 mM, as it is a tetravalent metal ion that is a compaction agent which can selectively precipitate RNA. It has high RNA affinity, but can be easily stripped from RNA molecules during RNA purification, without degrading the RNA molecules.

The wash buffers use high molecular weight PEG8000 at 5 to 20% (v/v), preferably 5 to 10% (v/v), to efficiently condense nucleic acids from the sample. Sodium chloride is used at 0.5 to 2 M, preferably 0.5 to 1 M, in the first wash buffer and 5 to 1000 mM, preferably 20 to 200 mM, in the second wash buffer to help to maintain the strength of the ionic medium and facilitate the release of cellular components into the solution. Ethylenediaminetetraacetic acid (EDTA) is a chelating agent used at 5 to 25 mM in the first wash buffer as it can help to inactivate nucleases and help to prevent degradation of DNA and RNA.

As described above, the first wash buffer used in the present magnetic bead based nucleic acid extraction system includes 0.5 to 3 M GuSCN, 5 to 20% (v/v) PEG8000, 0.5 to 2 M sodium chloride, 5 to 25 mM EDTA, and a non-ionic detergent selected from the group consisting of 0.25 to 4% (v/v) Ecosurf EH-9, 0.1 to 4% (v/v) Triton X-100, 0.25 to 4% (v/v) Tergitol 15-S-40 and mixtures thereof. The pH of the first wash buffer is adjusted to 3 to 5 with 1 M HCl. Optionally, 0.01 to 1% (v/v) lactic acid may also be added into the first wash buffer for adjusting the pH value. The three sets A, B and C of the first wash buffer are shown in the following Table 4 to Table 6.

TABLE 4

| First Wash Buffer Set A | |
| --- | --- |
| Component | Concentration range |
| Tris-HCl (pH 3 to 5) | 10 to 100 mM |
| PEG8000 | 5 to 20% (v/v) |
| Sodium chloride | 0.5 to 2M |
| EDTA | 5 to 25 mM |
| GuSCN | 0.5 to 3M |
| Lactic acid | 0.01 to 1% (v/v) |
| Ecosurf EH-9 | 0.25 to 4% (v/v) |

TABLE 5

| First Wash Buffer Set B | |
| --- | --- |
| Component | Concentration range |
| Tris-HCl (pH 3 to 5) | 10 to 100 mM |
| PEG8000 | 5 to 20% (v/v) |
| Sodium chloride | 0.5 to 2M |
| EDTA | 5 to 25 mM |
| GuSCN | 0.5 to 3M |
| Lactic acid | 0.01 to 1% (v/v) |
| Triton X-100 | 0.1 to 4% (v/v) |

TABLE 6

| First Wash Buffer Set C | |
| --- | --- |
| Component | Concentration range |
| Tris-HCl (pH 3 to 5) | 10 to 100 mM |
| PEG8000 | 5 to 20% (v/v) |
| Sodium chloride | 0.5 to 2M |
| EDTA | 5 to 25 mM |
| GuSCN | 0.5 to 3M |
| Lactic acid | 0.01 to 1% (v/v) |
| Tergitol 15-S-40 | 0.25 to 4% (v/v) |

As described above, the second wash buffer used in the present magnetic bead based nucleic acid extraction system includes 1 to 25 mM hexammine cobalt (III) chloride, 5 to 20% (v/v) PEG8000, 5 to 1000 mM sodium chloride, and a non-ionic detergent selected from the group consisting of 0.25 to 2% (v/v) ethylene oxide-propylene oxide copolymer mono(2-ethylhexyl) ether (Ecosurf EH-9, CAS number: 64366-70-7), 0.1 to 2% (v/v) 2-[4-(2,4,4-trimethylpentan-2-yl)phenoxy]ethanol (Triton X-100, CAS number: 9002-93-1, 0.25 to 2% (v/v) secondary alcohol ethoxylate (Tergitol 15-S-40, CAS number: 84133-50-6) and mixtures thereof. The pH of the second wash buffer is adjusted to 3 to 5 with 1 M HCl. Optionally, 0.01 to 1% (v/v) lactic acid may also be added into the second wash buffer for adjusting the pH value. The three sets A, B and C of the second wash buffer are shown in the following Table 7 to Table 9.

TABLE 7

| Second Wash Buffer Set A | |
| --- | --- |
| Component | Concentration range |
| Tris-HCl (pH 3 to 5) | 10 to 100 mM |
| PEG8000 | 5 to 20% (v/v) |
| Sodium chloride | 5 to 1000 mM |
| Hexammine cobalt (III) chloride | 1 to 25 mM |
| Lactic acid | 0.01 to 1% (v/v) |
| Ecosurf EH-9 | 0.25 to 2% (v/v) |

TABLE 8

| Second Wash Buffer Set B | |
| --- | --- |
| Component | Concentration range |
| Tris-HCl (pH 3 to 5) | 10 to 100 mM |
| PEG8000 | 5 to 20% (v/v) |
| Sodium chloride | 5 to 1000 mM |
| Hexammine cobalt (III) chloride | 1 to 25 mM |
| Lactic acid | 0.01 to 1% (v/v) |
| Triton X-100 | 0.1 to 2% (v/v) |

TABLE 9

| Second Wash Buffer Set C | |
| --- | --- |
| Component | Concentration range |
| Tris-HCl (pH 3 to 5) | 10 to 100 mM |
| PEG8000 | 5 to 20% (v/v) |
| Sodium chloride | 5 to 1000 mM |
| Hexammine cobalt (III) chloride | 1 to 25 mM |
| Lactic acid | 0.01 to 1% (v/v) |
| Tergitol 15-S-40 | 0.25 to 2% (v/v) |

Elution buffer is capable of releasing the nucleic acids from the magnetic beads. When the salt concentration in the buffer is low, the nucleic acid molecules have access to water molecules, resulting in their transitions to fully hydrated form during elution phase.

The elution buffer of the present disclosure has a pH of 8 provided by Tris-HCl, at which the bonds of the nucleic acids and the magnetic beads are destroyed, causing releasing of the nucleic acids from the magnetic beads.

In an embodiment, the optimal concentration for Tris-HCl (pH8) is 1 to 100 mM and the optimal concentration for EDTA is 1 to 25 mM. Adjust pH to 8 with 50 mM HCl if necessary. The formulation for the elution buffer of the present disclosure is shown in the following Table 10.

TABLE 10

| Elution Buffer | |
| --- | --- |
| Component | Concentration range |
| Tris-HCl (pH 8) | 1 to 100 mM |
| EDTA | 1 to 25 mM |

The associated protocol developed using the aforementioned buffers and the magnetic beads is capable of both DNA and RNA separate extraction as well as DNA and RNA simultaneous extraction from swab samples.

This system can be used with different types of magnetic beads with various coatings and particle sizes. The coatings of the magnetic beads may be but not limited to silica, polymer, carboxyl or PEG, and the particle sizes of the magnetic beads are ranged from 10 nm to 3 μm. This system can be used in manual purification as well as incorporated into device for automated preparation of the nucleic acids from the swab samples.

The present disclosure also provides the magnetic bead based nucleic acid extraction method using the aforementioned buffers and the magnetic beads. The following illustrates a procedure for manual extraction of the nucleic acids in a 1.5 ml Eppendorf tube on bench top with the lysis binding buffer, the first wash buffer, the second wash buffer and the elution buffer prepared according to the above embodiments.

1. Pipette 15 μl of the magnetic beads into a 1.5 ml Eppendorf tube.

2. Add 600 μl of the lysis buffer into the tube. Optionally, vortex or pipette the mixture for a short period of time until a uniform mixture is achieved.

3. Add 300 μl of the sample into the lysis buffer with the magnetic beads and resuspend the whole mixture until a uniform mixture is formed.

4. Leave the tube at room temperature for 4 minutes. Continuous agitation/resuspension is not needed.

5. Place the tube on the magnetic stand for 30 seconds or until the supernatant has cleared. Then carefully remove and discard the supernatant. (Note: The nucleic acid/beads complex sticks to the side of the Eppendorf tube with a visible dark gelatinous appearance.)

6. Remove the tube from the magnetic stand. Add 200 μl of the first wash buffer and resuspend the nucleic acid/beads complex until it disperses uniformly.

7. Place the tube on the magnetic stand and leave for 20 seconds or until the supernatant has cleared. Carefully remove and discard the supernatant.

8. Remove the tube from the magnetic stand. Add 200 μl of the second wash buffer and resuspend the nucleic acid/beads complex until it disperses uniformly.

9. Place the tube on the magnetic stand and leave for 20 seconds or until the supernatant has cleared. Carefully remove and discard the supernatant.

10. Remove the tube from the magnetic stand. Resuspend the nucleic acid/beads complex in 80 μl of the elution buffer until the suspension becomes homogeneous.

11. Incubate the mixture at 80° C. for 2 minutes and then briefly spin the tube to remove any liquid on the lid. Place the tube on the magnetic stand and leave for 20 seconds or until the supernatant has cleared.

12. The supernatant which contains the nucleic acids can now be transferred to a new tube and ready to be used in downstream reactions.

The following are examples illustrating the applications of nucleic acid extraction from different microorganisms using the magnetic bead based nucleic acid extraction method of the present disclosure.

In the following examples, the sample is prepared with viral transport medium (VTM) and swab simulation buffer. The formulation for swab simulation buffer is shown in the following Table 11. The experimental sample buffer includes 250 μl VTM and 50 μl swab simulation buffer (hereinafter referred as 300 μl experimental sample buffer).

TABLE 11

| Swab Simulation Buffer | |
| --- | --- |
| Component | Concentration |
| Porcine mucin | 2.5% (w/v) |
| Human whole blood | 1% (v/v) |
| NaCl | 0.85% (w/v) |
| PBS | 1x |
| Glycerol | 15% (v/v) |

Example 1 illustrates the manual extraction of RNA from human coronavirus virus OC43 (HCoV-OC43) using the buffer set A, which includes the lysis binding buffer set A, the first wash buffer set A, the second wash buffer set A, and the elution buffer of the present disclosure. 1 pfu of HCoV-OC43 was spiked in 300 μl experimental sample buffer, and then subject to the aforementioned extraction procedure using the buffer set A. 10 μl of the obtained eluate was used in a qPCR reaction for target detection of HCoV-OC43. FIG. 1 shows the amplification curves and Cq values of the qPCR assay in Example 1. The result demonstrated that the buffer set A can successfully extract RNA from HCoV-OC43 without affecting subsequent nucleic acid amplification and detection.

Figure 2:
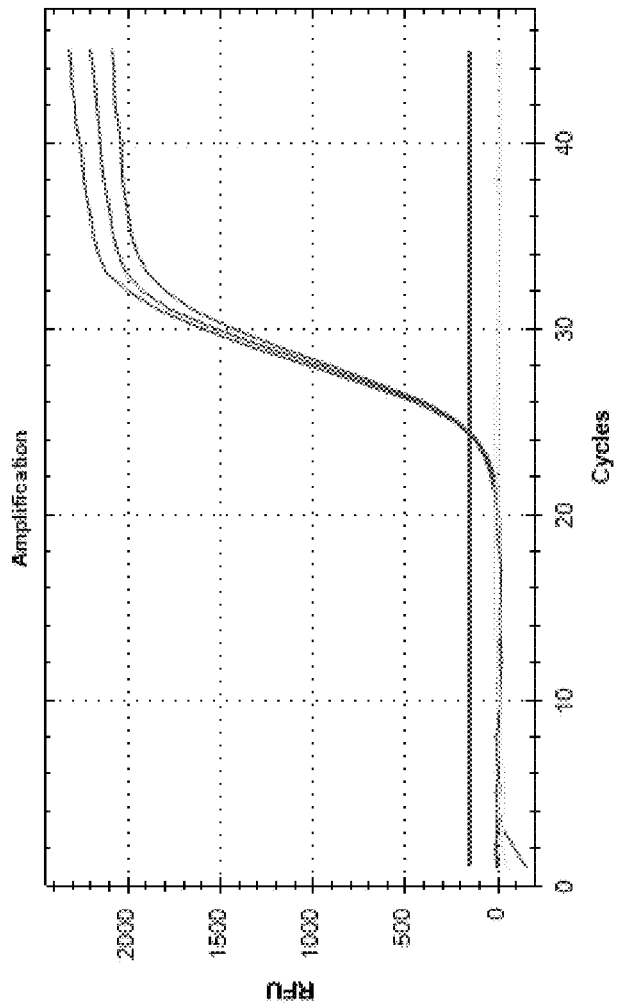
FIG. 2 shows the amplification curves and Cq values of the qPCR assay in Example 2.

Example 2 illustrates the manual extraction of DNA from *Staphylococcus aureus* (SA) using the buffer set A, which includes the lysis binding buffer set A, the first wash buffer set A, the second wash buffer set A, and the elution buffer of the present disclosure. 10^5 cfu of *Staphylococcus aureus* was spiked in 300 μl experimental sample buffer, and then subject to the aforementioned extraction procedure using the buffer set A. 10 μl of the obtained eluate was used in a qPCR reaction for target detection of *Staphylococcus aureus*. FIG. 2 shows the amplification curves and Cq values of the qPCR assay in Example 2. The result demonstrated that the buffer set A can successfully extract DNA from *Staphylococcus aureus* without affecting subsequent nucleic acid amplification and detection.

Figure 3:
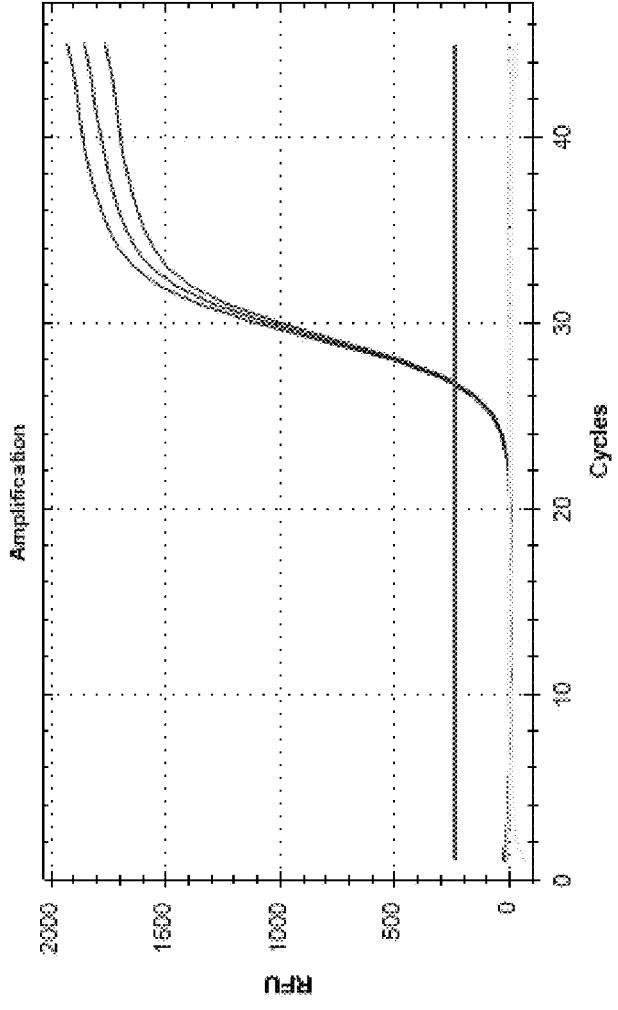
FIG. 3 shows the amplification curves and Cq values of the qPCR assay in Example 3.

Example 3 illustrates the manual extraction of DNA from Human adenovirus 3 (Ad3) using the buffer set A, which includes the lysis binding buffer set A, the first wash buffer set A, the second wash buffer set A, and the elution buffer of the present disclosure. 2500 pfu of Human adenovirus 3 was spiked in 300 µl experimental sample buffer, and then subject to the aforementioned extraction procedure using the buffer set A. 10 µl of the obtained eluate was used in a qPCR reaction for target detection of Human adenovirus 3. FIG. 3 shows the amplification curves and Cq values of the qPCR assay in Example 3. The result demonstrated that the buffer set A can successfully extract DNA from Human adenovirus 3 without affecting subsequent nucleic acid amplification and detection.

Figure 4:
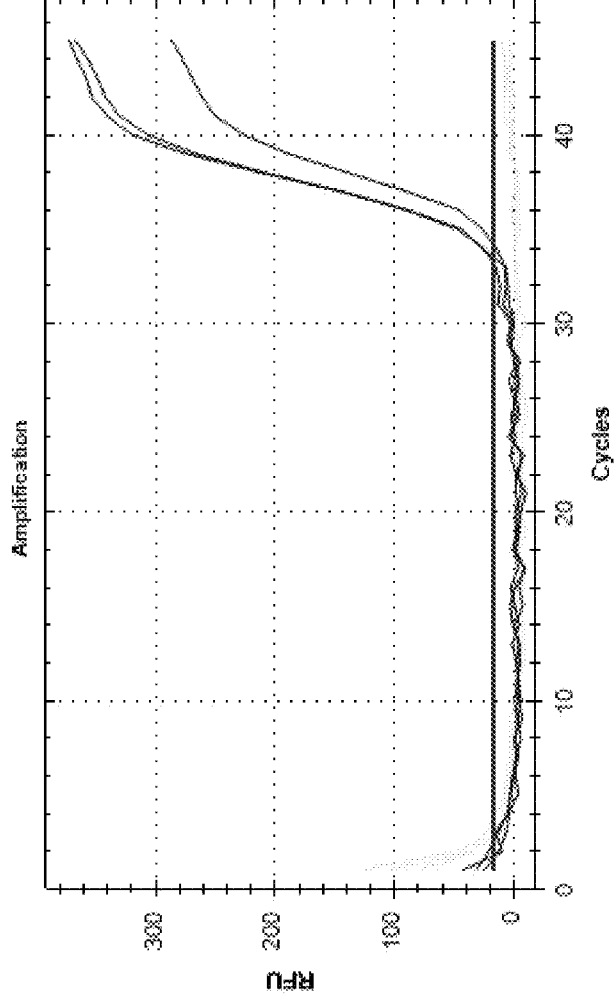
FIG. 4 shows the amplification curves and Cq values of the qPCR assay in Example 4.

Example 4 illustrates the manual extraction of RNA from human coronavirus virus OC43 (HCoV-OC43) using the buffer set B, which includes the lysis binding buffer set B, the first wash buffer set B, the second wash buffer set B, and the elution buffer of the present disclosure. 3×10^-4 pfu of HCoV-OC43 was spiked in 300 µl experimental sample buffer, and then subject to the aforementioned extraction procedure using the buffer set B. 10 µl of the obtained eluate was used in a qPCR reaction for target detection of HCoV-OC43. FIG. 4 shows the amplification curves and Cq values of the qPCR assay in Example 4. The result demonstrated that the buffer set B can successfully extract RNA from HCoV-OC43 without affecting subsequent nucleic acid amplification and detection.

Figure 5:
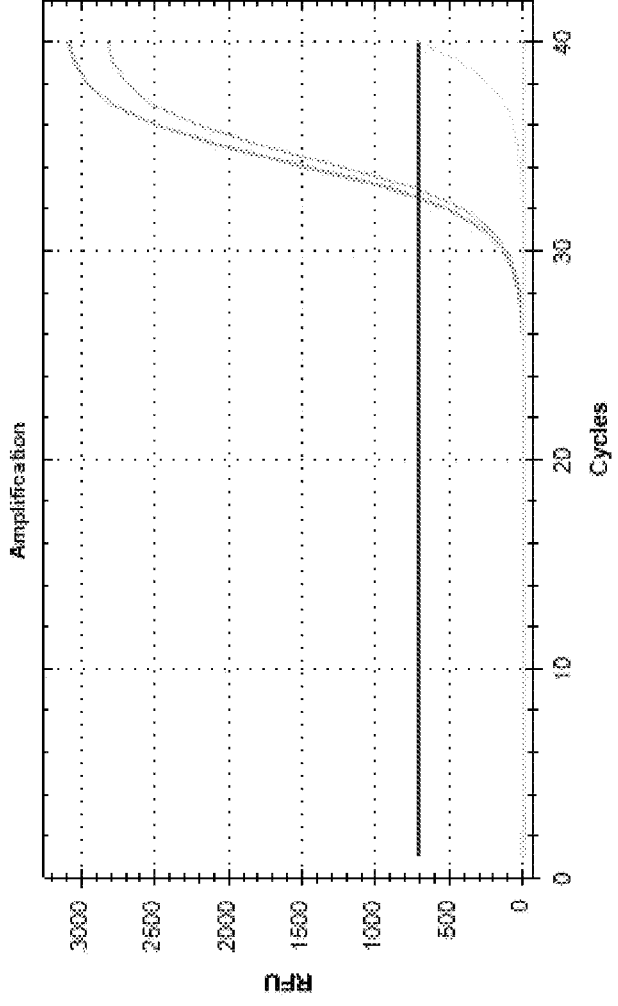
FIG. 5 shows the amplification curves and Cq values of the qPCR assay in Example 5.

Example 5 illustrates the manual extraction of DNA from *Staphylococcus aureus* (SA) using the buffer set B, which includes the lysis binding buffer set B, the first wash buffer set B, the second wash buffer set B, and the elution buffer of the present disclosure. 100 cfu of *Staphylococcus aureus* was spiked in 300 µl experimental sample buffer, and then subject to the aforementioned extraction procedure using the buffer set B. 10 µl of the obtained eluate was used in a qPCR reaction for target detection of *Staphylococcus aureus*. FIG. 5 shows the amplification curves and Cq values of the qPCR assay in Example 5. The result demonstrated that the buffer set B can successfully extract DNA from *Staphylococcus aureus* without affecting subsequent nucleic acid amplification and detection.

Figure 6:
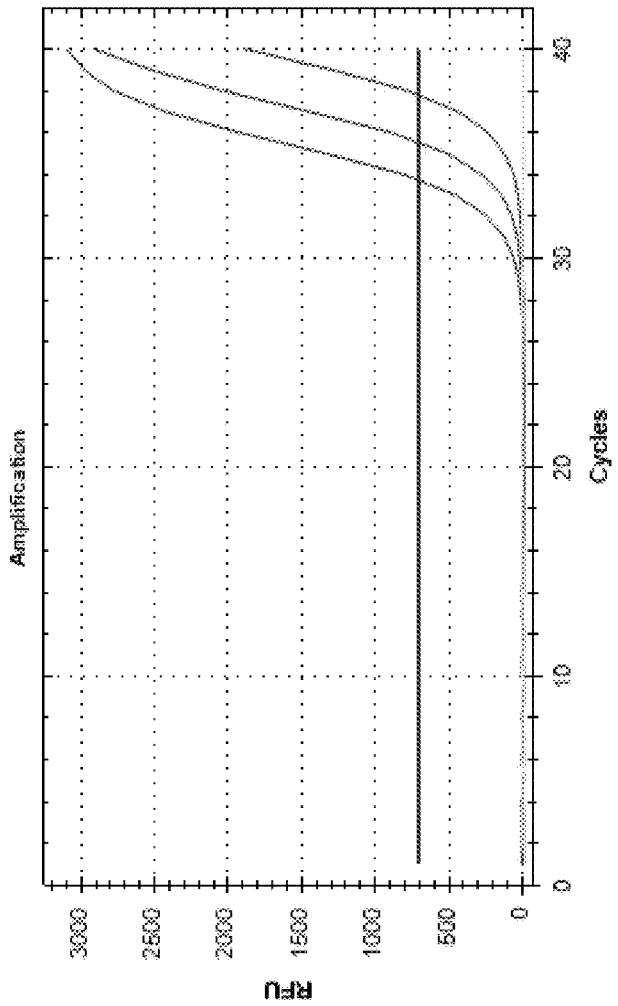
FIG. 6 shows the amplification curves and Cq values of the qPCR assay in Example 6.

Example 6 illustrates the manual extraction of DNA from Human adenovirus 3 (Ad3) using the buffer set B, which includes the lysis binding buffer set B, the first wash buffer set B, the second wash buffer set B, and the elution buffer of the present disclosure. 0.375 pfu of Human adenovirus 3 was spiked in 300 µl experimental sample buffer, and then subject to the aforementioned extraction procedure using the buffer set B. 10 µl of the obtained eluate was used in a qPCR reaction for target detection of Human adenovirus 3. FIG. 6 shows the amplification curves and Cq values of the qPCR assay in Example 6. The result demonstrated that the buffer set B can successfully extract DNA from Human adenovirus 3 without affecting subsequent nucleic acid amplification and detection.

Figure 7:
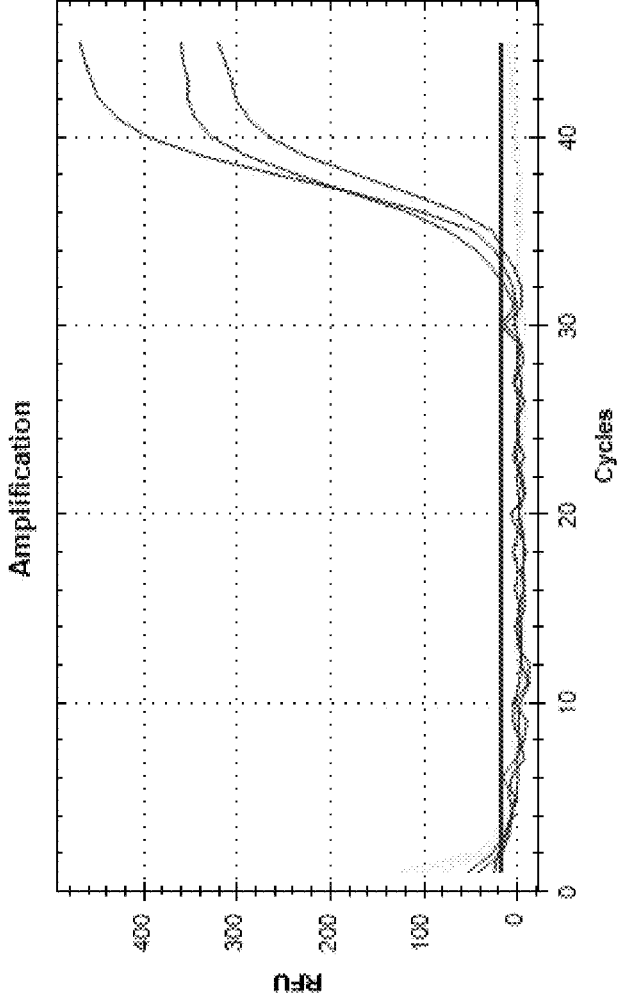
FIG. 7 shows the amplification curves and Cq values of the qPCR assay in Example 7.

Example 7 illustrates the manual extraction of RNA from human coronavirus virus OC43 (HCoV-OC43) using the buffer set C, which includes the lysis binding buffer set C, the first wash buffer set C, the second wash buffer set C, and the elution buffer of the present disclosure. 3×10^-4 pfu of HCoV-OC43 was spiked in 300 µl experimental sample buffer, and then subject to the aforementioned extraction procedure using the buffer set C. 10 µl of the obtained eluate was used in a qPCR reaction for target detection of HCoV-OC43. FIG. 7 shows the amplification curves and Cq values of the qPCR assay in Example 7. The result demonstrated that the buffer set C can successfully extract RNA from HCoV-OC43 without affecting subsequent nucleic acid amplification and detection.

Figure 8:
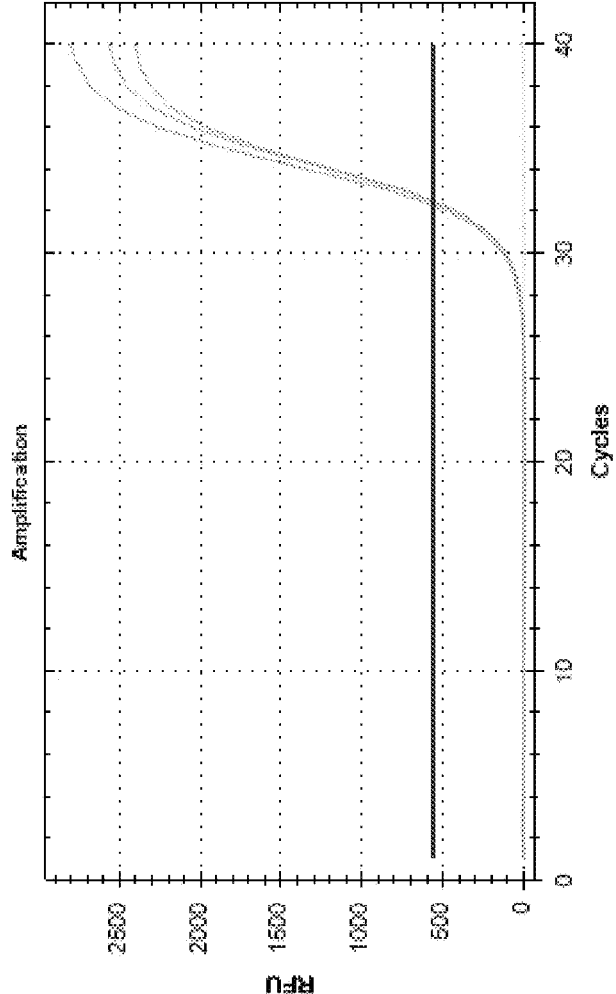
FIG. 8 shows the amplification curves and Cq values of the qPCR assay in Example 8.

Example 8 illustrates the manual extraction of DNA from *Staphylococcus aureus* (SA) using the buffer set C, which includes the lysis binding buffer set C, the first wash buffer set C, the second wash buffer set C, and the elution buffer of the present disclosure. 100 cfu of *Staphylococcus aureus* was spiked in 300 µl experimental sample buffer, and then subject to the aforementioned extraction procedure using the buffer set C. 10 µl of the obtained eluate was used in a qPCR reaction for target detection of *Staphylococcus aureus*. FIG. 8 shows the amplification curves and Cq values of the qPCR assay in Example 8. The result demonstrated that the buffer set C can successfully extract DNA from *Staphylococcus aureus* without affecting subsequent nucleic acid amplification and detection.

Figure 9:
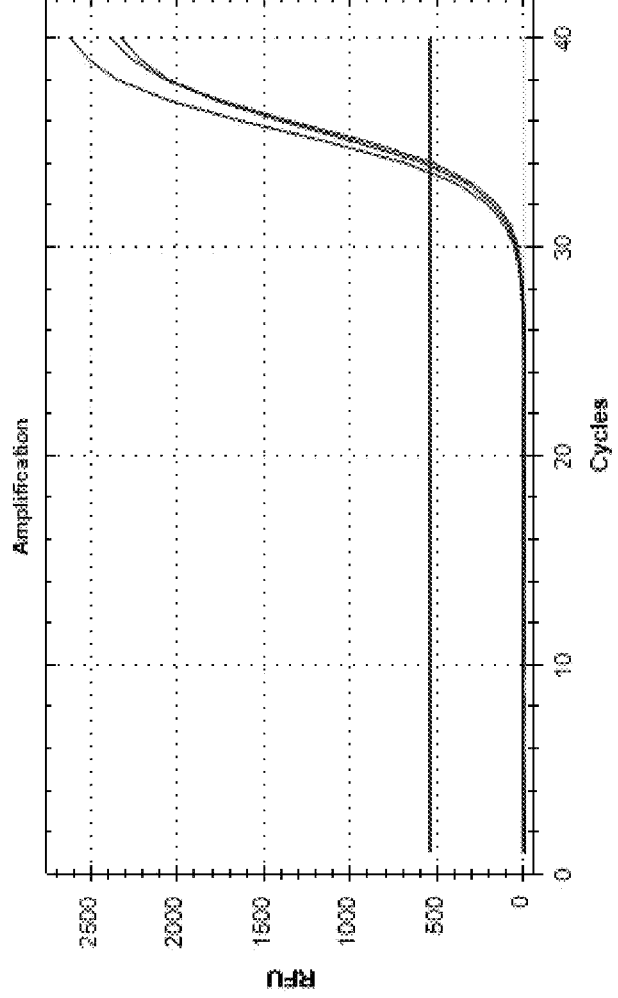
FIG. 9 shows the amplification curves and Cq values of the qPCR assay in Example 9.

Example 9 illustrates the manual extraction of DNA from Human adenovirus 3 (Ad3) using the buffer set C, which includes the lysis binding buffer set C, the first wash buffer set C, the second wash buffer set C, and the elution buffer of the present disclosure. 0.375 pfu of Human adenovirus 3 was spiked in 300 µl experimental sample buffer, and then subject to the aforementioned extraction procedure using the buffer set C. 10 µl of the obtained eluate was used in a qPCR reaction for target detection of Human adenovirus 3. FIG. 9 shows the amplification curves and Cq values of the qPCR assay in Example 9. The result demonstrated that the buffer set C can successfully extract DNA from Human adenovirus 3 without affecting subsequent nucleic acid amplification and detection.

Figure 10:
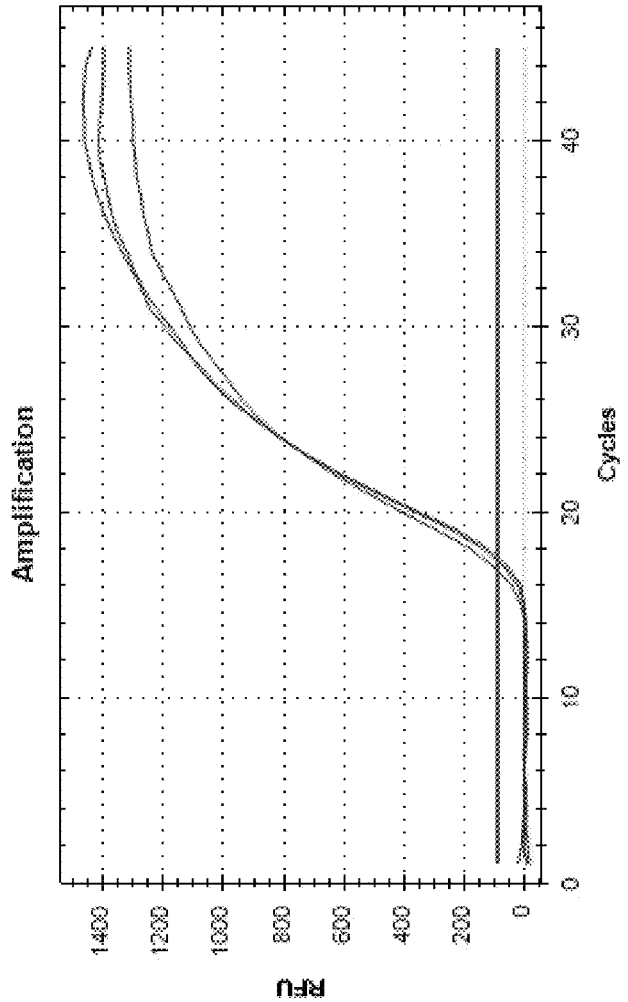
FIG. 10 shows the amplification curves and Cq values of the LAMP assay in Example 10.

Except PCR reaction, the compatibility of the present manual extraction system with LAMP reaction was also tested. Example 10 illustrates the manual extraction of RNA from human coronavirus virus OC43 (HCoV-OC43) using the present buffer system, wherein the extracted nucleic acids were detected by LAMP reaction. 0.1 pfu of HCoV-OC43 was spiked in 300 µl experimental sample buffer, and then subject to the aforementioned extraction procedure. 10 µl of the obtained eluate was used in a LAMP reaction for target detection of HCoV-OC43. FIG. 10 shows the amplification curves and Cq values of the LAMP assay in Example 10. The result demonstrated that the present buffer system is also compatible with LAMP reaction.

Figure 11A:
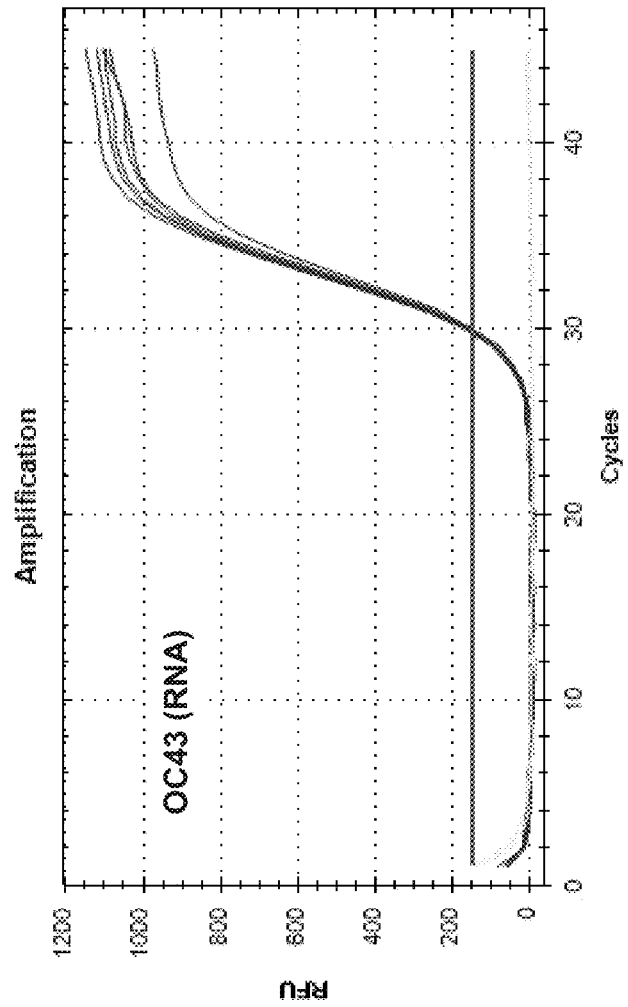
FIG. 11A and FIG. 11B show the amplification curves and Cq values of the qPCR assay in Example 11.
Figure 11B:
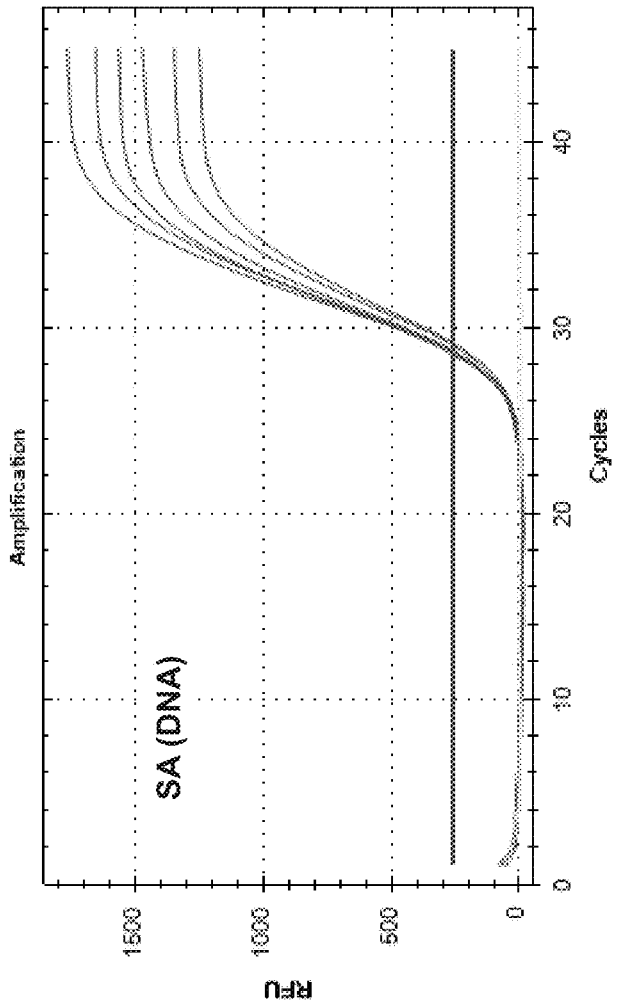

Example 11 illustrates the manual extraction of both DNA and RNA from human coronavirus virus OC43 (HCoV-OC43) and *Staphylococcus aureus* (SA) using the present buffer system. 0.1 pfu of HCoV-OC43 and 10^4 cfu of *Staphylococcus aureus* were co-spiked in 300 µl experimental sample buffer, and then subject to the aforementioned extraction procedure. 10 µl of the obtained eluate was used in a qPCR reaction for target detection of HCoV-OC43 and *Staphylococcus aureus*. FIG. 11A and FIG. 11B show the amplification curves and Cq values of the qPCR assay in Example 11. The result demonstrated that, except DNA and RNA separate extraction, the present buffer system is also capable of DNA and RNA simultaneous extraction.

Figure 12:
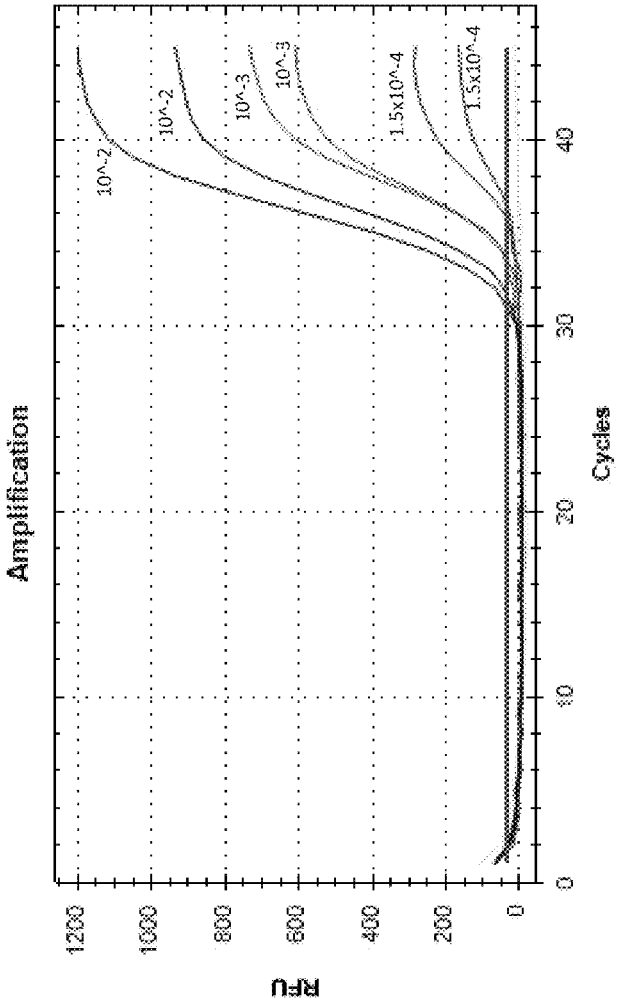
FIG. 12 shows the amplification curves and Cq values of the qPCR assay in Example 12.

Example 12 illustrates the manual extraction of RNA from human coronavirus virus OC43 (HCoV-OC43) at different concentrations using the present buffer system. 1.5× 10^-4 pfu, 10^-3 pfu and 10^-2 pfu of HCoV-OC43 were spiked in 300 µl experimental sample buffer, respectively, and then subject to the aforementioned extraction procedure. 10 µl of each obtained eluate was used in a qPCR reaction for target detection of HCoV-OC43. FIG. 12 shows the amplification curves and Cq values of the qPCR assay in Example 12. The result demonstrated that the present buffer system can extract RNA from HCoV-OC43 at low concentration.

Figure 13:
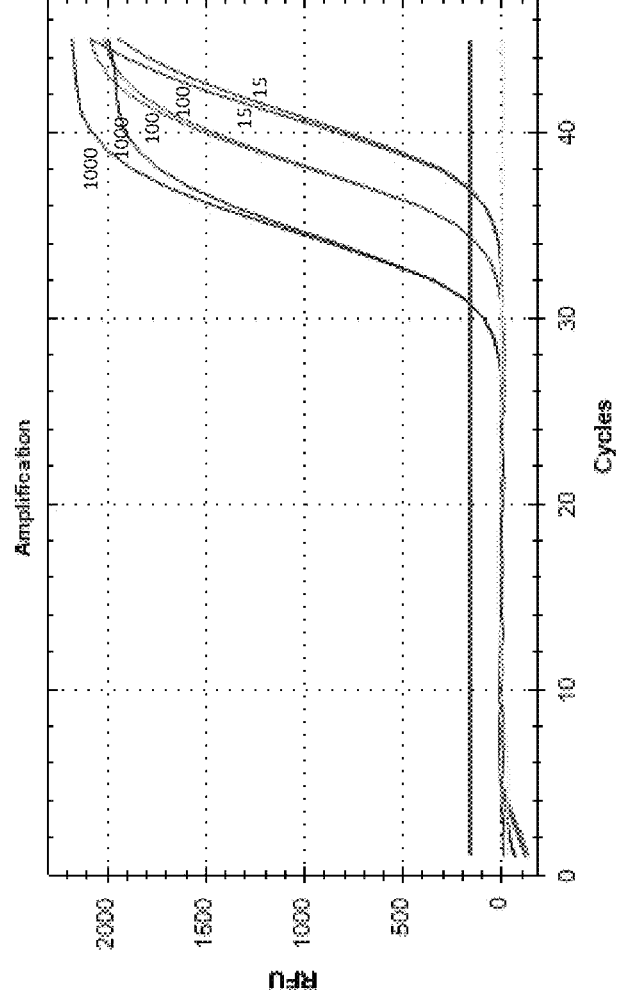
FIG. 13 shows the amplification curves and Cq values of the qPCR assay in Example 13.

Example 13 illustrates the manual extraction of DNA from *Staphylococcus aureus* (SA) at different concentrations using the present buffer system. 15 cfu, 100 cfu and 1000 cfu of *Staphylococcus aureus* were spiked in 300 μl experimental sample buffer, respectively, and then subject to the aforementioned extraction procedure. 10 μl of each obtained eluate was used in a qPCR reaction for target detection of *Staphylococcus aureus*. FIG. 13 shows the amplification curves and Cq values of the qPCR assay in Example 13. The result demonstrated that the present buffer system can extract DNA from *Staphylococcus aureus* at low concentration.

Figure 14:
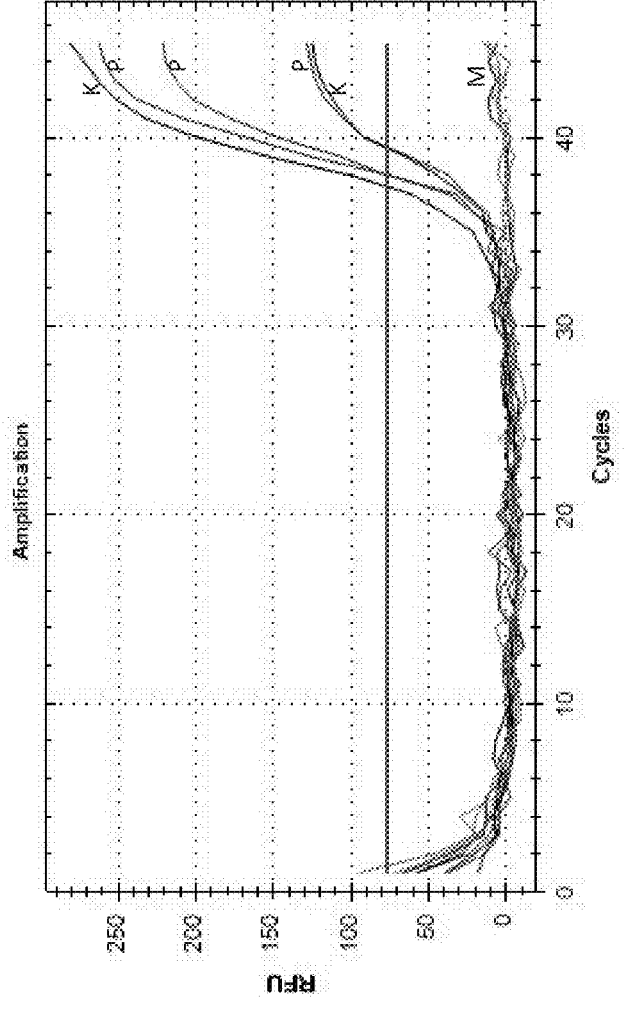
FIG. 14 shows the amplification curves and Cq values of the qPCR assay in Example 14.

Example 14 illustrates the comparison of RNA extraction from $1.5 \times 10^{\wedge}-4$ pfu of human coronavirus virus OC43 (HCoV-OC43) using the present protocol and the leading commercial kits. The present protocol is compared with Katsura Viral DNA/RNA Respi kit and Macherey-Nagel (MN) NucleoMag Pathogen kit. 10 μl of each obtained eluate was used in a qPCR reaction for target detection of HCoV-OC43. FIG. 14 shows the amplification curves and Cq values of the qPCR assay in Example 14. The result demonstrated that the present protocol has the best performance, followed by Katsura Viral DNA/RNA Respi kit and Macherey-Nagel NucleoMag Pathogen kit.

Figure 15:
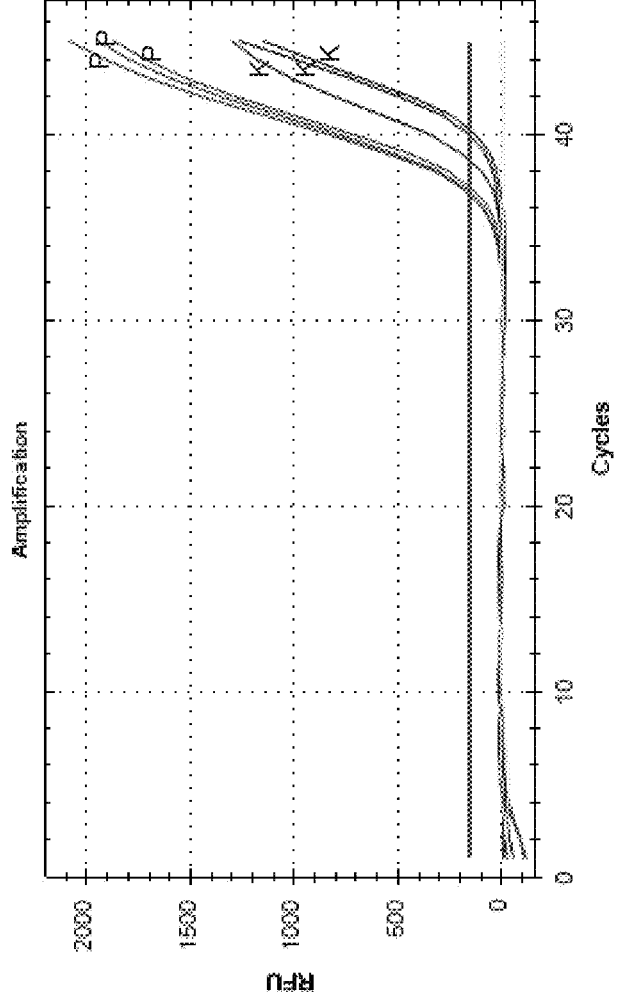
FIG. 15 shows the amplification curves and Cq values of the qPCR assay in Example 15.

Example 15 illustrates the comparison of DNA extraction from 15 cfu of *Staphylococcus aureus* (SA) using the present protocol and the leading commercial kit. The present protocol is compared with Katsura Viral DNA/RNA Respi kit. 10 μl of each obtained eluate was used in a qPCR reaction for target detection of *Staphylococcus aureus*. FIG. 15 shows the amplification curves and Cq values of the qPCR assay in Example 15. The result demonstrated that the present protocol has better performance compared with Katsura Viral DNA/RNA Respi kit.

FIG. 16 shows the comparison of nucleic acid extraction protocol turn-around-time for the present protocol and the leading commercial kits. As shown in FIG. 16, the turn-around-time for the present protocol is less than 10 minutes, which is shortest compared to the leading commercial kits.

FIG. 17 shows the feature comparison for the present protocol and the leading commercial kits. As shown in FIG. 17, the present protocol is alcohol-free, enzyme-free and only requires room temperature storage. There is no pretreatment or drying step in the present protocol and there is no centrifugation required in the present protocol. Further, the present protocol has the least total number of steps and the least amount of total time taken amongst the kits compared.

On the other hand, the compatibility of the present manual extraction system with different types of magnetic beads was also tested. The different types of the magnetic beads are shown in the following Table 12.

TABLE 12

| Types of magnetic beads | | |
| --- | --- | --- |
| Magnetic Bead | Coating | Particle size |
| A | Carboxyl | 10 nm |
| B | Carboxyl | 20 nm |
| C | Carboxyl | 200 nm |
| D | Silica, carboxyl modified | 300-500 nm |
| E | Silica | 10 nm |
| F | PEG1 | 10 nm |

TABLE 12-continued

| Types of magnetic beads | | |
| --- | --- | --- |
| Magnetic Bead | Coating | Particle size |
| G | Polymer | 1-3 um |
| H | Carboxyl | 0.8-1 μm |
| I | Silanol | 0.2-2 μm |
| J | Silica | 2-10 μm |

Figure 18A:
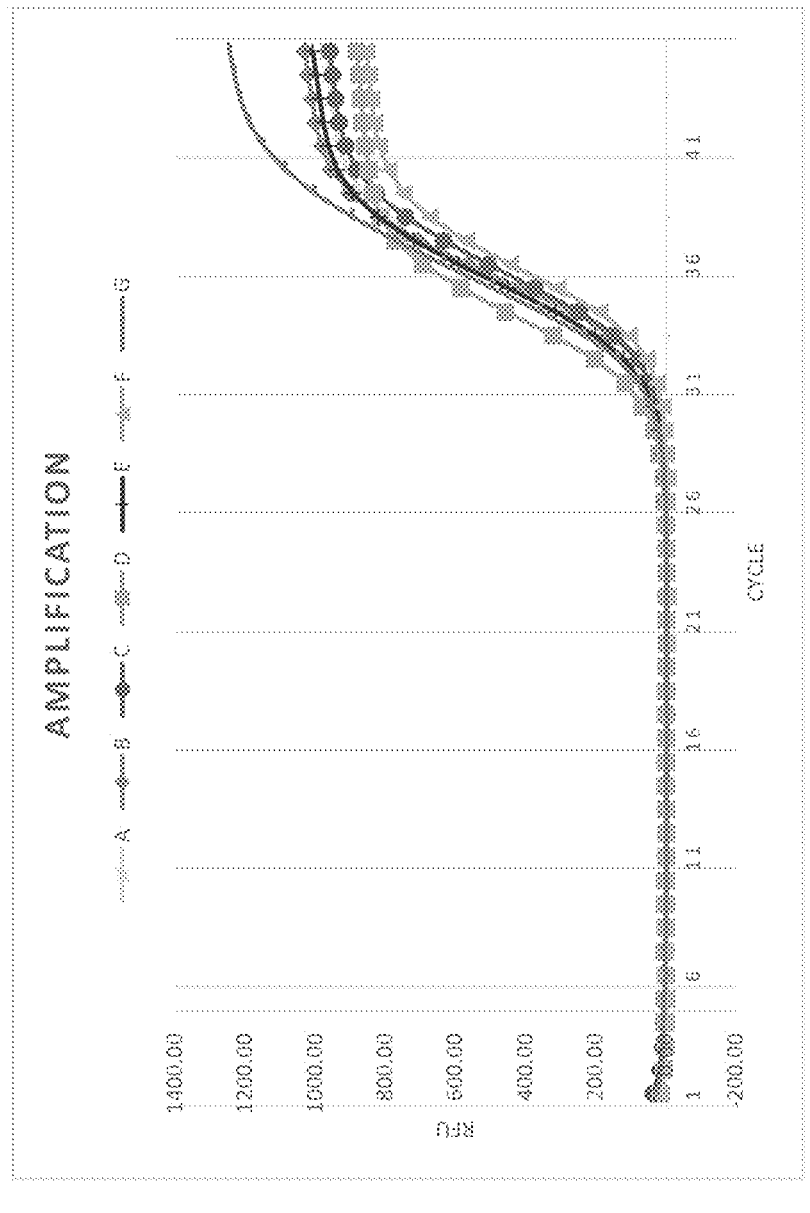
FIG. 18A and FIG. 18B show the amplification curves and Cq values of the qPCR assay using different types of magnetic beads for nucleic acid extraction.
Figure 18B:
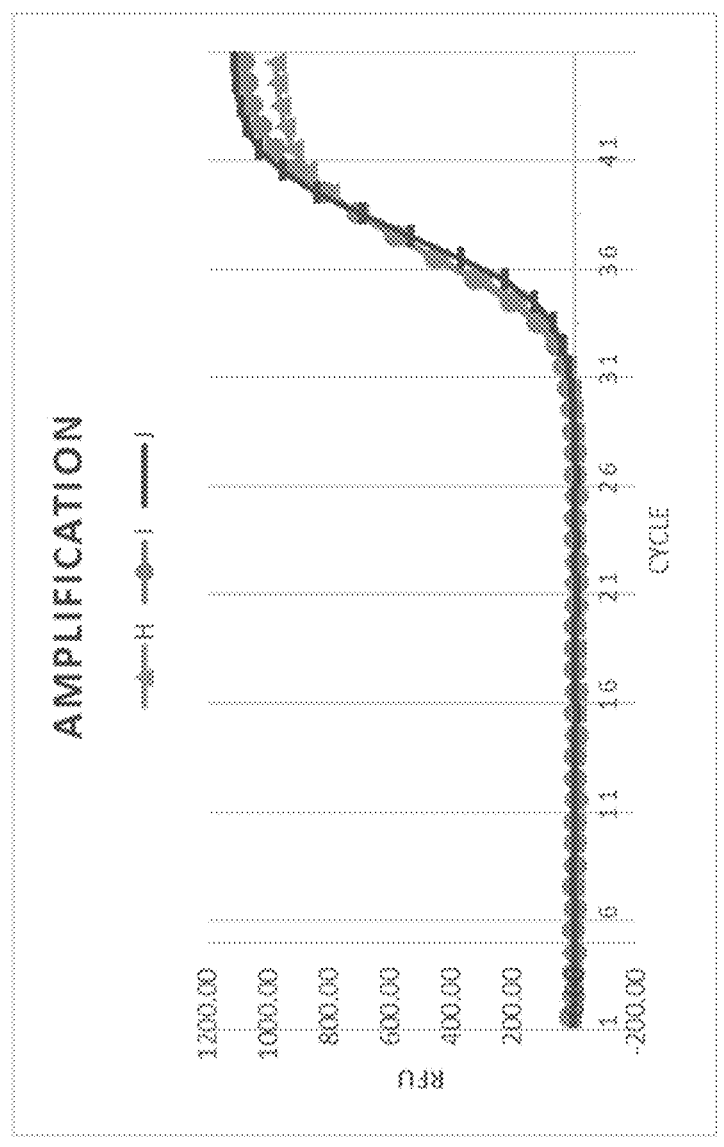

FIG. 18A and FIG. 18B show the amplification curves and Cq values of the qPCR assay using the different types of the magnetic beads for nucleic acid extraction. The result demonstrated that the present protocol can be used with different types of magnetic beads with various coatings and particle sizes.

Figure 19:
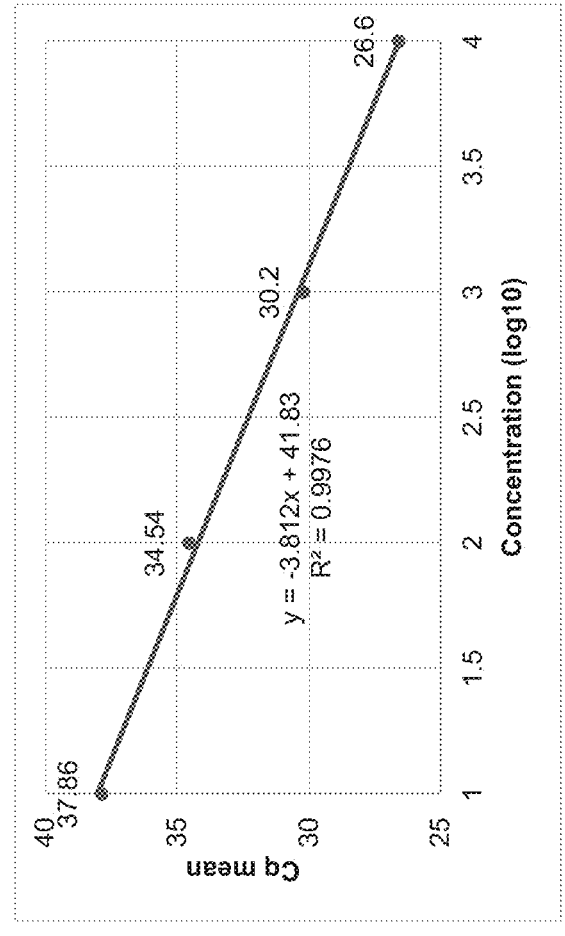
FIG. 19 shows the standard curve for yield using Vircell RNA with the present protocol on the automated nucleic acid extractor.

The present protocol is also ideal for automated nucleic acid extraction. For example, the present protocol can be applied on an automated nucleic acid extractor (M32 nucleic acid extractor, Katsura Biological Corp.). FIG. 19 shows the standard curve for yield using Vircell RNA with the present protocol on the automated nucleic acid extractor. The result showed an excellent linearity and demonstrated that the present protocol can be well incorporated into device for automated nucleic acid extraction.

Further, FIG. 20 shows the yield comparison using Vircell RNA with the present protocol on the automated nucleic acid extractor M32 with the leading commercial kit Qiagen viral RNA kit. The result demonstrated that the present protocol has good recovery rate compared to the leading commercial kit when tested using Vircell RNA.

From the above, the present disclosure demonstrates a novel nucleic acid extraction system with originally developed buffers and associated protocol to address the challenges encountered in the prior arts and to meet the requirement set out by WHO on the major features of point of care (POC) tests described by the acronym ASSURED criteria for affordable, sensitive, specific, user-friendly, rapid and robust, equipment-free, and deliverable to end-users.

Accordingly, the present disclosure provides a stable, user-friendly and environment-friendly, efficient and efficacious nucleic acid extraction and purification system optimal for pathogens from swab samples. The system includes the buffers, the magnetic beads and the protocol for nucleic acid extraction from swab samples. The buffers include the lysis binding buffer, the wash buffers and the elution buffer that are stable in storage at room temperature. The buffers include a special selection of the chaotropic salt, the detergent, the precipitant and other necessary components for ideal extraction of nucleic acids. The system is capable of lysis of the starting material, binding of the nucleic acids to the magnetic beads, washing of the inhibitors or debris and elution of the nucleic acids from the magnetic beads. The associated protocol is optimized to achieve efficient both DNA and RNA extractions, be it separately or simultaneously, from both virus and bacteria in swab samples.

Therefore, the magnetic bead based nucleic acid extraction system of the present disclosure has the following advantages.

1. User- and Environment-Friendly

The present disclosure does not include any corrosive, carcinogenic, toxic, harmful or inflammable components that would potentially have adverse effects on persons who handle or use it and environment where the components would be stored and used in. The present disclosure avoids the use of organic solvents, including ethyl alcohol, that are commonly used with other DNA isolation procedures.

2. Cost-Effective and Convenience to Transport, Store and Use

Originally formulated buffers and the magnetic beads used in the present disclosure are stable in storage at room temperature. The buffers are specially formulated without necessity to include enzymes that used for cell lysis especially for some bacteria that need harsh lysis condition and/or destroy of nucleases released after cell lysis, such as protease K. Exclusion of temperature sensitive components such as enzymes and carrier RNA/DNA, which usually require storage at −20° C., renders the present system stable when stored, transported and used at room temperature.

3. Short Turn-Around Time

The present disclosure uses the magnetic beads as a means to specifically bind nucleic acids once released from cell lysis and to hold them during washing steps to remove impurities. Separation of the magnetic beads from solutions under the force of magnet plate is superbly fast, happening within 30 seconds. Together with efficient cell lysis and elution, even manual extraction takes only less than 10 minutes compared to faster commercial kits which would take around half an hour.

4. Universal Recipe and Workflow for Both DNA and RNA from Pathogens in Swab Samples Including Viruses and Wide Spectrum of Bacteria The present disclosure is able to extract both DNA and RNA in separate samples or in one sample from variety of pathogens. This is better than most of the commercial kits which are for specific extraction of RNA or DNA from single type of pathogens (e.g., either virus or bacteria).

5. Great Potential for Automation and High Throughput

Most commercially available nucleic extraction kits call for a list of consumables and/or equipment to be provided by end-users, which can only be satisfied by well-facilitated labs and need additional centrifugation steps (e.g., column based method). Due to the technology of magnetic beads separation employed in the present disclosure, the whole process of nucleic acid extraction can be completed in one vessel, for example, one 1.5 mL Eppendorf tube in manual preparation. With the help of liquid handling system, both full automation and high throughput of sample processing can be realized.

6. Competitive Performance Compared to the Leading Commercial Nucleic Acid Extraction Kits Several commercial kits were used to compare extraction efficiencies. It was revealed that the present disclosure demonstrated comparable or better performance when compared with Katsura Viral DNA/RNA Respi kit, Macherey-Nagel NucleoMag Pathogen kit, and QIAamp Viral RNA Mini kit.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A magnetic bead based nucleic acid extraction system, comprising:
a plurality of magnetic beads, and
an alcohol-free buffer system, comprising:
a lysis binding buffer comprising 0.5 to 4 M GuSCN, 5 to 20% (v/v) PEG8000, 10 to 1000 mM sodium citrate, and a non-ionic detergent selected from the group consisting of 0.5 to 4% (v/v) nonylphenyl polyethylene glycol, 0.5 to 4% (v/v) secondary alcohol ethoxylate, 0.5 to 4% (v/v) ethylene oxide-propylene oxide copolymer mono(2-ethylhexyl) ether and mixtures thereof;
a first wash buffer comprising 0.5 to 3 M GuSCN, 5 to 20% (v/v) PEG8000, 0.5 to 2 M sodium chloride, 5 to 25 mM EDTA, and a non-ionic detergent selected from the group consisting of 0.25 to 4% (v/v) ethylene oxide-propylene oxide copolymer mono(2-ethylhexyl) ether, 0.1 to 4% (v/v) 2-[4-(2,4,4-trimethylpentan-2-ylphenoxy]ethanol, 0.25 to 4% (v/v) secondary alcohol ethoxylate and mixtures thereof;
a second wash buffer comprising 1 to 25 mM hexammine cobalt (III) chloride, 5 to 20% (v/v) PEG8000, 5 to 1000 mM sodium chloride, and a non-ionic detergent selected from the group consisting of 0.25 to 2% (v/v) ethylene oxide propylene oxide copolymer mono(2-ethylhexyl) ether, 0.1 to 2% (v/v) 2-[4-(2,4,4-trimethylpentan-2-yl phenoxy]ethanol, 0.25 to 2% (v/v) secondary alcohol ethoxylate and mixtures thereof; and
an elution buffer.

2. The magnetic bead based nucleic acid extraction system according to claim 1, wherein the pH value of the lysis binding buffer is 3 to 5.

3. The magnetic bead based nucleic acid extraction system according to claim 1, wherein the pH value of the first wash buffer is 3 to 5.

4. The magnetic bead based nucleic acid extraction system according to claim 1, wherein the first wash buffer further comprises 0.01 to 1% (v/v) lactic acid.

5. The magnetic bead based nucleic acid extraction system according to claim 1, wherein the pH value of the second wash buffer is 3 to 5.

6. The magnetic bead based nucleic acid extraction system according to claim 1, wherein the second wash buffer further comprises 0.01 to 1% (v/v) lactic acid.

7. The magnetic bead based nucleic acid extraction system according to claim 1, wherein the pH value of the elution buffer is 8.

8. The magnetic bead based nucleic acid extraction system according to claim 1, wherein the elution buffer comprises 1-25 mM EDTA.

* * * * *